United States Patent [19]
Mukai

[11] Patent Number: 5,785,056
[45] Date of Patent: Jul. 28, 1998

[54] PRESS-FITTING PRODUCT FOR A HUMAN BODY

[75] Inventor: Daisaku Mukai, Tokyo, Japan

[73] Assignees: Nippon Sigmax Co., Ltd.; Yukigaya Chemical Industry Co., Ltd., both of Tokyo, Japan

[21] Appl. No.: 819,003

[22] Filed: Mar. 17, 1997

[30] Foreign Application Priority Data

Apr. 1, 1996 [JP] Japan ................ 8-078683

[51] Int. Cl.⁶ .................................. A61G 15/00
[52] U.S. Cl. ..................... 128/845; 521/70; 128/846
[58] Field of Search ............................. 128/845, 846; 602/19; 5/636–648

[56] References Cited

U.S. PATENT DOCUMENTS

| | | |
|---|---|---|
| 847,775 | 2/1907 | Horn, Jr. . |
| 881,218 | 3/1908 | Bathrick . |
| 1,142,466 | 6/1915 | Stuart . |
| 1,381,336 | 6/1921 | Rehthaler . |
| 1,644,835 | 10/1927 | Howard . |
| 1,845,688 | 2/1932 | Untiedt . |
| 1,934,991 | 11/1933 | Mendez . |
| 2,100,029 | 11/1937 | Gammeter . |
| 2,626,886 | 1/1953 | Scholl . |
| 2,740,402 | 4/1956 | Scholl . |
| 2,742,038 | 4/1956 | Nelkin . |
| 4,294,239 | 10/1981 | Oram et al. . |
| 4,373,033 | 2/1983 | Gupta ........................ 521/70 |
| 4,556,441 | 12/1985 | Faasse, Jr. . |
| 4,991,573 | 2/1991 | Miller . |
| 5,060,639 | 10/1991 | Marcus . |
| 5,383,920 | 1/1995 | Sikes ........................ 602/23 |
| 5,437,618 | 8/1995 | Sikes ........................ 602/23 |

FOREIGN PATENT DOCUMENTS 0537910  3/1957  Canada ............................ 521/70

*Primary Examiner*—Michael A. Brown
*Attorney, Agent, or Firm*—Bacon & Thomas

[57] ABSTRACT

A press-fitting product for a human body such as a supporter is provided. The press-fitting product includes a base material constructed of continuous foam-type latex sponge, thereby providing the product with not only elasticity and restitutive force but also with air permeability.

2 Claims, 1 Drawing Sheet

PRESS-FITTING PRODUCT FOR A HUMAN BODY

BACKGROUND OF THE INVENTION

1. Field of the Invention

The present invention relates to a press-fitting product for a human body, and more particularly to a press-fitting product used for a human body such as a supporter or a lumbar pad widely used in the fields of sports and medical care.

2. Description of the Related Art

Generally, a press-fitting product for a human body such as a supporter requires lightness, elasticity (a feeling of fitting), air permeability, pleasant texture, moderate pressure and holding power (related to restitutive force of material), in view of overall fitting to a human body.

However, chloroprene rubber heretofore mainly used as the base material of a press-fitting product such as a supporter has drawbacks in that chloroprene rubber is massive, though it is provided with adequate elasticity and restitutive force, and that chloroprene rubber lacks air permeability, which has a great effect on comfortableness when a press-fitting product is fitted to a human body.

There are manufactured supporters and similar articles in which the above drawbacks are eliminated by using, as the base material, urethane sponge having air permeability. However, urethane sponge is inferior to chloroprene rubber in terms of a feeling of fitting and restitutive force of a product, and at present, such supporters or the like are far from satisfactory.

The present inventor conducted extensive studies relating to a press-fitting product provided with not only elasticity and restitutive force comparable to those of a press-fitting product such as a supporter made of chloroprene rubber, but also with excellent lightness and air permeability. As a result of the studies, the present inventor found that an extremely satisfactory result could be obtained if continuous foam-type latex sponge was used as a base material, and thus completed the present invention.

SUMMARY OF THE INVENTION

The present invention relates to a press-fitting product for a human body, including a base material constructed of continuous foam-type latex sponge.

DESCRIPTION OF THE PREFERRED EMBODIMENT

Figure 1:
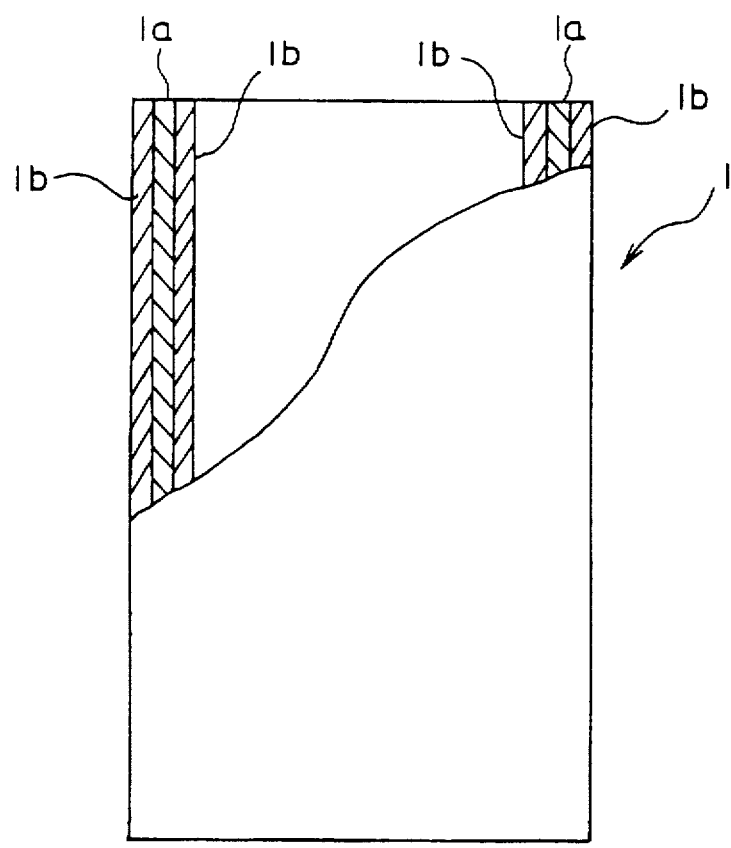
FIG. 1 is a front view of a supporter according to an embodiment of the present invention.

Continuous-foam latex sponge used in the present invention is provided with air permeability, and preferable materials for such sponge include continuous foam of natural rubber or continuous foam of synthetic rubber, particularly acrylonitrile-butadiene rubber and styrene-butadiene rubber.

If the expansion ratio of such foam is between 4:1 to 7:1 and the thickness is between 1 and 5 mm, there can be obtained an air permeability of 3.0 $cm^3/cm^2/S$ or more, as measured in accordance with a measurement method provided in JIS L1096, and this provides comfort to a person to whom such a press-fitting product is fitted. The lower the expansion ratio and the thicker the foam, the lower its elasticity and air permeability. On the other hand, the higher the expansion ratio and the thinner the foam, the weaker its pressure and holding power, and such foam is unsuitable for a press-fitting product. Incidentally, the above expansion ratio can be calculated using the following relation:

$$\text{Expansion ratio} = \frac{\text{Material (capacity)} + \text{Air (capacity)}}{\text{Material (capacity)}}$$

For continuous foam-type latex sponge, it is preferable to use sponge which further includes an antibacterial agent such as thiabendazole (TBZ), so as to obtain a press-fitting product provided with antibacterial properties.

A press-fitting product according to the present invention is manufactured by adhering together such latex sponge for the base material and another material such as jersey made of nylon and polyester, then, cutting and sewing the materials according to a conventional method.

Embodiment of the Invention

The present invention will be further described while referring to the drawing showing an embodiment.

Reference number 1 denotes a supporter. Continuous-foam latex sponge formed of hexaploid foam of acrylonitrile-butadiene rubber is used as base material 1$a$, and the supporter is constituted cylindrically by three-layer material formed by adhering jersey 1$b$ made of nylon on both sides of the continuous foam-type latex sponge 1$a$.

According to the present invention, there is provided a press-fitting product for a human body such as a supporter which is provided not only with elasticity and restitutive force comparable to those of the conventional supporter made of chloroprene rubber, but also with air permeability which the conventional supporter made of chloroprene rubber cannot provide, and there can be realized an extremely comfortable state in which such a light press-fitting product provided with adequate holding power is fitted to a human body without giving a stuffy feel.

What is claimed is:

1. A press-fitting product for a human body comprising a base material constructed of continuous foam-type foam made of natural rubber, acrylonitrile-butadiene rubber or styrene-butadiene rubber, wherein the expansion ratio of foam is between 4:1 and 7:1 and the thickness of the foam is between 1 and 5 mm.

2. The press-fitting product for a human body comprising a base material constructed of continuous foam-type foam made of natural rubber, acrylonitrile-butadiene rubber or styrene-butadiene rubber, as claimed in claim 1, which product is constituted cylindrically by three-layer material formed by adhering jersey made of nylon or polyester on both sides of the base material.

* * * * *